US010849942B2

(12) United States Patent
Mattey

(10) Patent No.: US 10,849,942 B2
(45) Date of Patent: Dec. 1, 2020

(54) TREATMENT OF BACTERIAL INFECTIONS IN AQUACULTURE

(71) Applicant: Fixed Phage Limited, Glasgow (GB)

(72) Inventor: Michael Mattey, Glasgow (GB)

(73) Assignee: Fixed Phage Limited, Glasgow (GB)

( * ) Notice: Subject to any disclaimer, the term of this patent is extended or adjusted under 35 U.S.C. 154(b) by 0 days.

(21) Appl. No.: 15/567,825

(22) PCT Filed: Apr. 20, 2016

(86) PCT No.: PCT/EP2016/058809
§ 371 (c)(1),
(2) Date: Oct. 19, 2017

(87) PCT Pub. No.: WO2016/170013
PCT Pub. Date: Oct. 27, 2016

(65) Prior Publication Data

US 2018/0110812 A1 Apr. 26, 2018

(30) Foreign Application Priority Data

Apr. 20, 2015 (EP) .................................... 15164343

(51) Int. Cl.

| | |
|---|---|
| ***C12N 1/00*** | (2006.01) |
| ***A61K 35/76*** | (2015.01) |
| ***A23K 50/80*** | (2016.01) |
| ***A23K 20/163*** | (2016.01) |
| ***A23K 20/195*** | (2016.01) |
| ***A61K 47/61*** | (2017.01) |
| ***A61K 47/62*** | (2017.01) |
| ***A61K 47/69*** | (2017.01) |
| ***A61P 31/04*** | (2006.01) |
| ***A61K 9/00*** | (2006.01) |
| ***C12N 7/00*** | (2006.01) |

(52) U.S. Cl.
CPC ............ *A61K 35/76* (2013.01); *A23K 20/163* (2016.05); *A23K 20/195* (2016.05); *A23K 50/80* (2016.05); *A61K 9/0053* (2013.01); *A61K 47/61* (2017.08); *A61K 47/62* (2017.08); *A61K 47/6921* (2017.08); *A61P 31/04* (2018.01); *C12N 7/00* (2013.01); *C12N 2795/00032* (2013.01)

(58) Field of Classification Search
None
See application file for complete search history.

(56) References Cited

U.S. PATENT DOCUMENTS

2005/0220770 A1 10/2005 Scott et al.

FOREIGN PATENT DOCUMENTS

| | | | |
|---|---|---|---|
| WO | 2006/047872 | 5/2006 | |
| WO | WO-2006047872 A1 * | 5/2006 | ........... A23L 3/3463 |
| WO | 2013/000093 | 1/2013 | |
| WO | WO-2013000093 A1 * | 1/2013 | ............. A61K 35/76 |
| WO | 2014/049008 | 4/2014 | |

OTHER PUBLICATIONS

Christiansen et al. Applied and Environmental Microbiology vol. 80, No. 24 Dec. 1, 2014 (Year: 2014).*
International Search Report and Written Opinion, International Patent Application No. PCT/EP2016/058809, dated Jul. 22, 2016.
International Preliminary Report on Patentability, International Patent Application No. PCT/EP2016/058809, dated Jul. 12, 2017.
Christiansen Roi Hammershaimb et al: "Detection and quantification of Flavobacterium psychrophilum-specific bacteriophages in vivo in rainbow trout upon oral administration: implications for disease control in aquaculture" Applied and Environmental Microbiology, American Society for Microbiology, vol. 80, No. 24, pp. 7683-7693.

* cited by examiner

*Primary Examiner* — Jana A Hines
*Assistant Examiner* — Khatol S Shahnan Shah
(74) *Attorney, Agent, or Firm* — Casimir Jones, SC; Robert A. Goetz

(57) ABSTRACT

A composition comprises bacteriophage covalently attached to an edible particle and is for use in treating bacterial infection in fish or crustaceans. Infections in fish or crustaceans caused by *Vibrio, Aeromonas, Yersinia, Moritella, Rickettsia, Piscirickettsia, Lactococcus, Pseudomonas, Flavobacterium* or *Photobacterium* bacteria species can be treated. Bacteria infected with a lysogenic bacteriophage are used for treating disease of fish or crustaceans caused by similar infections by bacteria carrying lysogenic bacteriophage that express a toxin gene.

13 Claims, 8 Drawing Sheets

| | 0s UV | 15s UV | 30s UV | 45s UV |
|---|---|---|---|---|
| Free phages | 100 | 0.21 | 0.23 | 0.18 |
| Immobilised phages | 100 | 22 | 17 | 13 |

TREATMENT OF BACTERIAL INFECTIONS IN AQUACULTURE

FIELD OF THE INVENTION

The present invention relates to treatment of bacterial infections in aquaculture, generally farmed production of shrimp, prawns and fish. In particular the invention relates to compositions and methods for reducing or preventing infections and/or for treating existing infections in such aquaculture.

BACKGROUND OF THE INVENTION

Bacteriophages are the most numerous form of life on Earth. They can be found in all environments where bacteria grow. Bacteriophages are detected in ground and surface water, soil, food (e.g., sauerkraut, wine), sewage and sludge. They have also been isolated from humans and animals, for example from faeces, urine, saliva, spit, rumen and serum. Bacteriophages are able to penetrate different organs and tissues, including the central nervous system, and are a part of intestinal flora together with their bacterial hosts. They are responsible for 10-80% of total bacterial mortality in aquatic ecosystems and are an important factor limiting bacterial populations.

Therapeutic applications of bacteriophage are known. WO 03/093462 discloses methods for the immobilisation of viruses, in particular bacteriophages, whilst retaining their biological activity for use as antibacterial agents. Given that the natural environment of bacteriophages is aqueous it has been widely assumed that stability towards dehydration as disclosed in WO 03/093462 tends towards the natural stability in aqueous media.

Oceans and inland waters are largely fished to their limit and the supply of wild-caught fish peaked in the 1990s. With the global wild fish supply stagnant and the human population increasing, new research shows that farmed fish and shellfish production will have to increase by 133 percent between 2010 and 2050 in order to meet projected fish demand worldwide.

Nearly one-third of the world's seafood is produced by industrial aquaculture and production has increased by 6% per year from 8.7 million tons of fish in 1990 to 50 million tons in 2011 and projected to reach 80 million tons by 2030. Fish farming plants, however, often suffer from heavy financial losses due to the development of infections caused by microbial pathogens, including multidrug resistant bacteria that are easily transmitted through water and therefore able to infect a great variety of fish species.

Although pathogenic species have been described in the majority of bacterial taxonomic groups, only a relatively small number are responsible for significant economic losses. Vibriosis and photobacteriosis are primarily diseases of marine and estuarine fish, both in natural and commercial production systems throughout the world, occurring infrequently in freshwater fish. Both diseases can cause significant mortality in fish, reaching values of up to 100% in infected facilities. Vibriosis and photobacteriosis are caused by bacteria from the family Vibrionaceae. Vibriosis is caused by species of *Vibrio*, namely by *Vibrio anguillarum*.

Others species of *Vibrio*, such as *V. alginolitycus, V. carchariae, V. salmonicida, V. damsela, V. ordalii, V. parahemolyticus* and *V. vulnificus*, also cause important infections in several species of fish. Photobacteriosis is caused by *Photobacterium damselae* subsp. *piscicida* which is a highly pathogenic bacterium that does not seem to have host specificity, infecting a diverse range of fish species. Other bacteria including *Aeromonas salmonicida*, causative agent of furunculosis, *Rickettsia*-like bacteria, *Cytophaga marina, Flavobacterium psychrophilum* and *Pseudomonas plecoglossicida* are also important groups of fish pathogens.

Diseases like EMS (Early Mortality Syndrome) of shrimps are caused by bacterial infections in which the bacterium (*Vibrio parahaemolyticus*) is itself infected by a lysogenic bacteriophage which carries a toxin gene. On bacteriophage infection the bacterium incorporates the bacteriophage into its genome and expresses the toxin which leads to EMS in the shrimp.

Although vaccination is the ideal method to prevent many different kinds of infectious diseases it is not always applicable in fish species.

Chemotherapy is a rapid and effective alternative method to treat or prevent bacterial infections, but the frequent use of antibiotics has resulted in an increasing drug-resistance in pathogenic bacteria in the aquaculture, agriculture and medical areas and since few chemotherapeutic drugs are licensed for use in fisheries alternative treatments are required.

Nakai et al. *Diseases of Aquatic Organisms*, vol. 37, pp. 33-41, (23 Jun. 1999) describes the effect of treating *Lactococcus garvieae* infection in yellowtail through the use of bacteriophage to which *L. garvieae* is susceptible. Nakai et al. report that each of the three bacteriophage isolates they tested for stability in natural (unsterilised) sea water persisted for 3 days but had perished within 1 week. Nakai et al. also describe the use of fish food impregnated with $10^{7.9}$ PFU $g^{-1}$ of bacteriophage. Giving this food to fish that were subsequently challenged with $10^{8.5}$ CFU of *L. garvieae* by anal intubation decreased the mortality rate of the challenged fish.

WO 2006/047872 discloses antibacterial compositions comprising bacteriophage that are adsorbed onto a matrix. The composition may be added to a feed for aquatic use.

Bacteriophage have been proposed for various treatments of bacterial infection. It is known, however, that bacteriophages survive only for relatively short periods in their natural environment, i.e. in water. Average decay rates of viruses in natural seawater samples can be calculated, based on well-known data, e.g. in *C H Suttle* (*Microb. Ecol.* (1994) 28: 237-243, at about 0.48 $day^{-1}$. The greatly reduced survival of bacteriophages in natural aqueous environments is due to a combination of causes, significantly predation and sunlight.

Hence, there is a need for an alternative means to treat or reduce bacterial infections of farmed crustaceans, especially shrimp and prawns, and fish.

Object of the Invention

An object of the present invention is to provide compositions and uses of those compositions and methods using those compositions that offer an alternative treatment of bacterial infections in commercially reared crustaceans, e.g. prawns and shrimp, and/or fish. A further aim of particular embodiments is to provide improved such compositions, uses and methods.

SUMMARY OF THE INVENTION

A composition comprising bacteriophage covalently attached to a particle is for use in treating bacterial infection in fish or crustaceans. Edible particles are preferably used. The present invention is based upon enhancement of stability and viability of bacteriophage in aqueous environments, rendering possible treatment of bacterial infections in aquaculture.

Feed for crustaceans or fish is provided, comprising bacteriophage covalently attached to a particle for treating bacterial infection in fish or crustaceans.

A method of making fish or crustacean feed comprises mixing bacteriophages covalently attached to particles into feed components, to produce feed comprising said particles.

Bacteria infected with a lysogenic bacteriophage are provided and can be used in treating disease of fish or crustaceans.

DETAILS OF THE INVENTION

A composition of the invention accordingly comprises bacteriophage covalently attached to a particle for use in treating bacterial infection in fish or crustaceans. After administration to the fish or crustaceans, for example via feed containing the particles, bacterial infections are treated.

The particle can be a carrier particle, made e.g. of edible material or an inert material, in which case the carrier particle is typically approximately spherical. It may have an average diameter of up to 1 mm, up to 100 microns, up to 50 microns, up to 10 microns, from 1 nm, from 10 nm, from 100 nm, from 0.5 microns or any combinations of these. In specific examples below, particles in the range 1 to 200 microns were used. The particles in general can be approximately round or spheroid; they are preferably smooth. Particles or fragments of edible material may also be of irregular shapes and sizes.

Particle size is suitably measured using methods and apparatus recognized as standard in the art. Particle sizing in dispersions can be accomplished using a variety of techniques, including laser diffraction, dynamic light scattering (DLS), disc centrifugation, and light microscopy. All of these techniques have their advantages and limitations. Laser diffraction relies on a well-controlled presentation of the sample to the measurement region and is limited to samples with narrow range of particle concentrations. Dilution is often required and this may affect the particle size, particularly in compounds with high solubility. Examples of sizing equipment are made by Malvern Instruments (UK), using laser diffraction methods. For highly irregular particles, the diameter refers to the greatest diameter in any dimension even if the particle is relatively non-spherical.

In embodiments of the invention, bacteriophages covalently attached to a plurality of particles are provided. These are preferably in relatively homogenous form, in which a large proportion, preferably substantially all, of the plurality of particles have diameters in the stated range, more preferably 80% or more, 90% or more or 95% or more of the particles with phage covalently attached have diameters in the stated range (being any range as set out above or elsewhere herein).

Particles for use in the invention to which bacteriophage are immobilised by covalent bonding are generally edible by or substantially inert to the animal to be treated. In examples, nylon particles (beads) were used. Other inert, preferably non-toxic biocompatible material may be used. In addition, the particle may be made of a biodegradable material. Suitable materials include polymethyl methacrylate, polyethylene, ethylene/acrylate copolymer, nylon-12, polyurethane, silicone resin, silica and nylon 1010. WO 2003/093462 describes further materials that the particles may be made from.

Immobilisation or attachment of bacteriophage to the particle substrate may be achieved in a number of ways. Preferably, bacteriophage are immobilised via covalent bonds formed between the bacteriophage coat protein and the carrier substrate.

Further, bacteriophage are preferably immobilised to the substrate via their head groups or nucleocapsid by activating the substrate particle before the addition and bonding of bacteriophage.

The term “activated/activating/activation” is understood to mean the activation of the substrate such as electrically, e.g. by corona discharge, or by reacting said substrate with various chemical groups (leaving a surface chemistry able to bind viruses, such as bacteriophage head or capsid groups).

Activation of said substrate may be achieved by, for example, preliminary hydrolysis with an acid, preferably HCl followed by a wash step of water and an alkali to neutralise the acid. Preferably, said alkali is sodium bicarbonate. Binding of bacteriophage via their head groups is advantageous. In the case of complex bacteriophage for example, binding via head groups leaves the tail groups, which are necessary for bacteria-specific recognition, free to infect, i.e., bind and penetrate a host bacterial cell. A plurality of various strain-specific bacteriophage may be immobilised to a substrate at any one time.

Coupling of phage to a substrate is as a result of the formation of covalent bonds between the viral coat protein and the substrate such as through an amino group on a peptide, for example a peptide bond. “Coupling Agents” that aid this process vary, and are dependent on the substrate used. For example, for coupling to nylon or other polymers with amino or carboxy surface groups the coupling agents carbodiimide or glutaraldehyde may be used.

Further details of methods and preferred methods for covalent attachment of bacteriophage to particles or pellets or feed components, retaining phage infectivity, are described in more detail in WO 2003/093462 and WO 2007/072049.

A further option is to use particles that comprise one or more targeting moiety, e.g. a protein or ligand, to direct the particles to desired targets within fish or crustaceans.

For example, particles can comprise one or more lectins to target them e.g. to fish gills for treatment e.g. of *Yersinia* infection.

Suitably the present invention delivers bacteriophage via feed and the particle is made of edible material. Hence it is conveniently incorporated in feed for fish/crustaceans. Bacteriophage can be attached to particles of carbohydrate (e.g. cellulose) or protein (including fish protein or animal protein) and this can be achieved using for example electric discharge methods of application to nylon beads.

Feed comprising the particles may comprise carbohydrate, protein, lipid, vitamin or a mixture of one or more of all.

The invention is of use in treatment of diseases of fish and crustaceans caused by the following bacteria:

| Bacteria | Marine hosts | Diseases |
|---|---|---|
| *Vibrio* species: | Crustaceans | Vibriosis |
| *V. harveyi* | Fish | Necrotising hepatopancreatitis |
| *V. fluvialis* | | (EMS) |
| *V. parahaemolyticus* | | Various other infections |
| *V. vulnificus* | | |
| *V. alginolyticus* | | |
| *V. penaeicida* | | |
| *V. anguillarum* | | |
| *V. carchariae* | | |

-continued

| Bacteria | Marine hosts | Diseases |
|---|---|---|
| *V. salmonicida* | | |
| *V. damsela* | | |
| *V. ordalii* | | |
| *V. owensii* | | |
| *Aeromonas* species: | Fish | Furunculosis |
| *A. salmonicida* | | |
| *A. hydrophilla* | | |
| *A. punctata* | | |
| *Yersinia ruckeri* | Fish | Enteric redmouth disease |
| *Moritella viscosa* | Fish | Winter ulcer disease |
| *Rickettsia salmonis* | Salmon | Salmon rickettsial syndrome |
| *Piscirickettsia salmonis* | | (SRS) |
| *Lactococcus garvieae* | Fish | Lesions of vascular endothelium |
| *Pseudomonas plecoglossicida* | Ayu fish | Haemorrhagic ascites |
| *Flavobacterium psychrophilum* | Fish | Bacterial cold water disease (BCWD) |
| *Photobacterium damselae* | Fish | Photobacteriosis |

In one preferred application of the invention the bacteriophage are for use in treating bacterial infection in crustaceans; more specifically, for treating infection by *Vibrio* bacteria species.

*V. parahaemolyticus* is a common inhabitant of coastal and estuarine environments all over the world. Hence they are often found naturally associated with shrimp aquaculture systems. Certain environmental conditions may be more favourable for the establishment, survival and growth of the organism such as temperature, salinity, zooplankton, tidal flushing and dissolved oxygen.

*V. parahaemolyticus* is closely related to shrimp pathogenic luminous bacteria such as *V. harveyi, V. campbelli* and *V. owensii*. These along with other closely related *Vibrio* spp form a "*V. harveyi* clade". Bacteria within this clade have a very high degree of similarity at phenotypic and genotypic level. Certain strains of *V. parahaemolyticus* can cause gastroenteritis in humans and clinical strains are characterised by the ability to produce a thermostable direct hemolysin (TDH) or a TDH-related hemolysin (TRH). The genes encoding these hemolysins (tdh and trh genes) are generally used as markers for human pathogenic strains of *V. parahaemolyticus*. Human pathogenic strains possessing these markers account for 1-2 percent of environmental strains of *V. parahaemolyticus*. All strains (both clinical and environmental) produce a thermolabile hemolysin (TLH) encoded by tlh gene and this is generally used as a marker for *V. parahaemolyticus* in diagnostic tests (48). The tdh and trh genes encoding the virulence factors are present in "pathogenicity islands", which are discrete genetic units present only in virulent strains; having a Guanine+Cytosine (G+C) content that is different from the rest of the chromosomal DNA and are generally acquired by horizontal gene transfer.

By use of the invention with bacteriophage specific to *Vibrio* species these infections of e.g. shrimp and prawn can now be treated.

In another preferred application of the invention, the bacteriophage are for treating bacterial infection in fish, especially for treating infection by *Vibrio, Aeromonas, Yersinia, Moritella, Rickettsia, Piscirickettsia, Lactococcus, Pseudomonas, Flavobacterium* or *Photobacterium* bacteria species. Useful bacteriophage are disclosed e.g. in US 2013/0323209.

Feed for fish and crustaceans, especially shrimp and prawns, is provided by the invention. One aspect of these embodiments of the invention hence provides feed for crustaceans or fish, comprising bacteriophages covalently attached to particles for treating bacterial infection in fish or crustaceans.

It is preferred that all of the feed is edible and so it is preferred that the particle is made of edible material, e.g. carbohydrate or protein as described elsewhere herein. Mixed in with the particles are other feed components that typically include carbohydrate, protein, lipid, vitamin or a mixture of one or more of all.

Another aspect of these embodiments of the invention hence provides feed for crustaceans or fish to which bacteriophage is covalently attached, for treating bacterial infection in fish or crustaceans. Typically, the feed contains edible feed components to which bacteriophage are covalently attached. As per previous embodiments, bacteriophage may be covalently attached to carbohydrate or protein of the feed.

In particular embodiments of the invention, illustrated in the examples below, feed pellets are provided to which the bacteriophage are covalently attached, generally to the outer surface thereof by methods in which pellets are activated then have phage attached. Suitable and preferred pellet sizes are as described elsewhere herein.

Specific pellets of the invention, with bacteriophage covalently attached are for treating infection by *Vibrio* bacteria species in crustaceans.

Other specific pellets of the invention, with bacteriophage covalently attached are for treating infection by *Vibrio, Aeromonas, Yersinia, Moritella, Rickettsia, Piscirickettsia, Lactococcus, Pseudomonas, Flavobacterium* or *Photobacterium* bacteria species in fish.

Bacteriophage for the invention include bacteriophage in general without limitation provided that the bacteriophage is obtainable and its host or target bacteria can be cultured and infected in culture. The bacteriophage can be ssRNA, dsRNA, ssDNA or dsDNA bacteriophage, with either circular or linear arrangement of the genetic material. The suitable bacteriophage include Myoviridae, Siphoviridae, Podoviridae, Lipothrixviridea, Rudiviridae, Ampullaviridae, Bacilloviridae, Bicaudaviridae, Clavaviridae, Corticoviridae, Cystoviridae, Fusseloviridae, Globuloviridae, Guttavirus, Inoviridae, Leviviridae, Microviridae, Plasmaviridae and Tectiviridae. Suitable phage for use in embodiments mentioned above infect and are lytic for the bacterial families and species mentioned.

Examples of how to isolate desired phage are widespread in the literature, including just by way of illustration: Gill J J and Hyman P, " Phage choice, isolation, and preparation for phage therapy", Curr Pharm Biotechnol., 2010, Jan.;11 (1): pp2-14, and the previously mentioned "Bacteriophage Therapy" minireview by Sulakvelidze et al., *Antimicrobial Agents and Chemotherapy*, March 2001, pp 649-659.

The invention extends the viability of both lytic and lysogenic bacteriophages in their natural environment, sea, fresh water or other aqueous environments, by covalent immobilisation. Surprisingly increased viability and stability have been illustrated in examples below and now make possible the bacterial treatments set out herein.

Immobilisation has been found in examples set out below in more detail to make predation more difficult. Predation can occur through enzymatic digestion with extracellular or intracellular enzymes from bacteria or fungi, from ingestion by protozoa and subsequent digestion or from the digestive processes of other eukaryotic organisms.

In general, advantages of the invention stem from the unexpected extension of phage viability in saline waters, fresh waters and other predominately aqueous environments; unexpected resistance to degradation by components of natural environment; unexpected resistance to predation—achieved by the use of bacteriophage covalently attached to particles in feed as described herein.

A method of the invention comprises combining pellet components with particles to which bacteriophage are covalently attached, to form feed comprising the particles. That feed is then for use to deliver the bacteriophage to the target fish/crustaceans.

In a particular method of making fish or crustacean feed, the steps comprise mixing bacteriophages covalently attached to particles into feed components, to produce feed comprising said particles.

The method may comprise:

(a) combining feed components to form a mixture,
(b) treating the mixture to (i) increase its moisture content, or (ii) heat and cook the mixture, or (iii) both (i) and (ii), and
(c) subsequently adding the particles to the treated mixture and, optionally, forming pellets of feed.

Heat can be used to achieve at least partial sterilization of the pellets. One method of the invention comprises:

(b) heat treating the mixture,
(c) cooling the treated mixture, and
(d) subsequently adding the particles to the treated and cooled mixture.

This order of steps avoids applying heat to and thus damaging the bacteriophage component of the feed.

In certain methods the particles are added to formed pellets. This may be achieved by spraying pellets with a solution or suspension of the particles. The sprayed pellets can then be dried to adhere the particles thereto.

In an example of the method, preparation of the pellets comprises:

1) mixing pellet components,
2) pulverising mixed components to reduce particle size,
3) conditioning the mixture, by exposing the pulverised components to water and/or steam,
4) forming pellets from the conditioned mixture,
5) cooling the pellets,
6) drying the pellets,
7) adding bacteriophage on particles to the pellets, and
8) transferring the pellets to a container, typically a bag.

Typically the pellet components comprise a mixture of one or more or all of proteins, fats, carbohydrates, minerals, vitamins and water (e.g. meat or fish meal, wheat flour, rice bran, rice pollard, split peas, corn, soya meal, mill mix, fish oil, vitamin and mineral premix etc.). Similar mixes are used for both crustaceans and fish, though specific tailored mixes are also used.

The conditioning step can be used to increase the water content and/or to partially or completely cook pellet components. Steam is generally used, which effectively cooks the components and increases moisture content at the same time. Depending upon the steam heat and step duration some degree of sterilisation may also occur at this time.

Pellets are generally formed by passing the conditioned material through a pelletizing mill. Pellet size varies and the pulverising step can be of longer duration or more vigorous if the end pellets are to be of smaller sizes. Depending on the size of the fish/crustaceans, pellet diameters are typically in the range 0.1 to 30 mm, more generally 0.5 mm or greater, also more generally up to 25 mm, up to 20 mm, up to 15 mm, up to 10 mm or up to 8 mm. Pellet sizes under 2 mm normally require fairly extensive pulverisation to be carried out. Shrimp pellets are more commonly in the range approximately up to 5 mm or 8 mm, and can be smaller, say up to 2 mm or 3 mm. Fish pellets are larger and more commonly of diameter 3 mm upwards.

Pellet components usually include starch. However, in water the pellets disintegrate due to the starch swelling. Conditioning at lower temperatures has been shown to reduce the starch expansion and provide a way of maintaining pellet integrity while wet. An optional step is to add a second heating step after the pelletizing step.

Heating after milling, where conventionally the cooling process can occur, has two main effects:

1) Starch is converted to digestible form,
2) Wheat gluten binding the pellet becomes substantially insoluble (other glutens have been shown to be unsuccessful).

The use of this post-milling conditioning step dramatically improves the stability of the pellet in water. Formulation cost is saved because less binder needs to be added and this tremendously helps digestibility for marine life.

Pellet buoyancy can be altered dependent on whether the marine life targeted are top or bottom feeders. Hollow pellets allow significantly longer flotation times.

Still further provided by the invention are methods of making fish or crustacean feed comprising covalently attaching bacteriophage to feed pellets.

As per embodiments in the examples below, which contain greater details, one such method comprises forming feed components into pellets, and treating the pellets to covalently attach bacteriophage thereto. Pellet treatment is suitably described elsewhere herein, for activation of pellets then covalent attachment of phage. Electrical based are especially suitable. In an example corona discharge has been successfully used. Activated pellets can then be combined with phage, e.g. by bringing the pellets into contact with a solution or suspension of phage.

In a separate aspect of the invention, it is possible to take advantage of cellular factors that prevent superinfection of bacteria already infected with a lysogenic bacteriophage by a second bacteriophage of the same type. Accordingly, the invention provides bacteria infected with a lysogenic bacteriophage for use in treating disease of fish or crustaceans. A method of preventing disease in fish or crustaceans comprises infecting the same with this bacteria.

In use, fish or crustaceans are hence deliberately infected with this bacteria, known to be relatively prevalent but relatively innocuous (as the bacteriophage with which it is infected is lysogenic and does not cause disease). This step, however, prevents disease caused by bacteria being subsequently infected with bacteriophage carrying a toxin gene. The presence of the first bacteriophage infection means superinfection by more pathogenic bacteriophage is reduced.

The bacteria are for example *Vibrio* bacteria for use in treating disease of crustaceans.

The bacteria is for example a *Vibrio, Aeromonas, Yersinia, Moritella, Rickettsia, Piscirickettsia, Lactococcus, Pseudomonas, Flavobacterium* or *Photobacterium* bacteria species for use in treating disease of fish.

Feed for crustaceans or fish, comprising these bacteria, form further embodiments of the invention.

EXAMPLES

The invention is now illustrated in the following specific embodiments with reference to the accompanying drawings in which:

FIG. 1 shows survival of bacteriophage ϕlin 24 in various aqueous environments, FIG. 2 shows immobilised bacteriophage are more resistant to UV exposure, FIG. 3 shows storage stability of *Peptobacterium* single phage immobilised onto cellulose, FIG. 4 shows storage stability of *Peptobacterium* single phage immobilised onto copolymer beads, FIG. 5 shows survival of free and immobilised bacteriophage when exposed to stress conditions (wet, dry, UV and high temperature), FIG. 6 shows survival of free and immobilised bacteriophage in the presence of the potato plant antifungal agent Neozil, FIG. 7 shows survival of free and bacteriophage immobilised onto cellulose strips in soil, FIG. 8 shows survival of free and bacteriophage immobilised onto nylon strips in soil, FIG. 9 shows survival of *Peptobacterium* phage treated cellulose powder following incubation in non-sterile soil, FIG. 10 shows infectious activity of *Peptobacterium* phage treated cellulose powder following incubation in non-sterile soil, FIG. 11 shows antibacterial activity displayed when multiple bacteriophage types are immobilised on nylon in the presence of susceptible and non-susceptible host bacteria, FIG. 12 shows infectious activity of *Salmonella* bacteriophage immobilised onto alginate sheets, FIG. 13 shows clearing zones around pellets of the invention, and FIG. 14 shows the survival of shrimp challenged with *Vibrio parahaemolyticus* after their being fed with pellets with bacteriophage covalently attached thereon or control pellets.

EXAMPLE 1

We tested bacteriophage covalently attached to both plastic (nylon) and carbohydrate (cellulose) particles to prove the feasibility of using compositions of the invention in aquaculture applications.

It was first determined whether bacteriophages immobilised on to cellulose powder survive longer than free bacteriophages in both sea water and fresh water. FIG. 1 shows the survival of immobilised and non-immobilised Bacteriophage ϕlin 24 in sea water. Bacteriophage ϕlin 24 immobilised on cellulose powder survived significantly longer than non-immobilised bacteriophages in sea water ($P \leq 0.001$).

Procedures

Media and Methods

Table 1—All media was made and methods were performed in accordance with the appropriate standard operating procedure (SOP).

TABLE 1

| Medium/Method | SOP |
|---|---|
| Nutrient Agar | Agar 50 |
| Nutrient Broth | Broth 51 |
| Immobilisation of phage | Immobilisation |
| Culture of bacteria | Culture |

"Agar 50" SOP

Weigh desired amount of powder

Add powder to empty bottle of adequate size

Add distilled water to desired volume

Cap loosely and seal with autoclave tape over the lid.

Autoclave at 121° C. for 15 minutes in accordance with the manual

Leave media to cool

Preparation of nutrient agar plates

Place set media in microwave.

autoclave for 5 minutes check media has completely melted. If not microwave for a further 1 minute.

Place bottle of media in water bath (50° C.) and leave to cool.

pour media into petri plates with approximately 15 mL media per plate.

allow to dry

"Broth 51" SOP

Weigh desired amount of powder

Place distilled water to desired volume in a beaker with a magnetic stirrer

Add powder to water and allow to dissolve

Add desired amount to a clean bottle

Cap loosely and seal with autoclave tape over the lid.

Autoclaving the media

Place bottle of media in autoclave

Switch on autoclave at 121° C. for 15 minutes in accordance with the manual

Leave media to cool

Once cool label appropriately

Leave on shelf until further use.

"Immobilisation" SOP

Applicable bacteriophages

ϕ K

ϕ Gamma

ϕ PLS27 HER200

ϕ 7 LINDBERG HER4

ϕ 24 LINDBERG HER4

ϕ FC3-9 HER111

ϕ K13 HER173

ϕ 68HER49

ϕ MINCE

ϕ 235

ϕ CLYDE

ϕ 11575

ϕ 1173

ϕ T4 10360

ϕ T7 10380

ϕ Psp1

Materials required

Bacteriophage culture

Bunsen Burner

Pipette for measuring 0-100 μl

Sterile 0-200 μl beveled tips

Sterile plastic spreader 30 ml Universal plastic container

Pipette controller

Sterile 10 ml stripettes

Use of corona discharge machine (flatbed)

Ensure corona machine is OFF before cleaning/sterilizing.

Hook the clear cover to hold open.

Wipe corona table with 70% alcohol to sterilise. The electrode above should also be wiped.

Allow the alcohol to dry off for 2 minutes. Then close the hood.

Start the ozone extractor.

Switch the table on

Switch the corona machine on

Place the material on the middle of the corona table.

Close the lid

Start the corona treatment by pushing "start" on the table controls.

The surface of the film will be treated.
As soon as treatment is complete switch the corona machine off
Open the cover
Coat material in bacteriophage solution and spread using a sterile spreader.
Place the material in a sterile plate
Put all switches in the "off" position
Clean the table and electrode with 70% alcohol.
Washing material
The material should be washed 3 times in PBS
Allow the material to air dry in a laminar hood for 2 hours.
Antibacterial activity assay
Prepare agar overlays
A square of treated material is carefully placed on top of the set agar layer
The plate is incubated face up.
Following incubation a clearing zone around the material can be quantified.
"Culture" SOP
Appropriate Bacteria
*Staphylococcus aureus*
*Escherichia coli*
*Klebsiella* sp.
*Enterobacter* sp.
*Pseudomonas aeruginosa*
*Bacillus cereus*
*Acinetobacter baumannii*
Equipment and Materials required
Nutrient broth
Sterile culture loop.
Bacterial culture cultured on nutrient agar
Black marker pen.
37° C. rotating incubator.
Bunsen burner.
Sterile 30 ml Universal container
Preparation of Bacteria
Label the side of 30 ml Universal container with the operator name, date and microorganism cultured.
Turn Bunsen burner onto high flame.
Remove the lid of the Universal 30 ml container.
Add 15 ml of sterile nutrient broth to the sterile Universal 30 ml container.
Close lid of the Universal 30 ml container.
Remove sterile loop from plastic wrap.
Remove lid from petri dish containing nutrient agar and bacterial culture.
Remove a single colony by applying the sterile loop to the colony gently.
Place lid on petri dish.
Remove lid from Universal 30 ml container containing nutrient broth.
Add culture loop containing the bacterial colony to the nutrient broth for 2 seconds.
Remove and discard culture loop in biohazard box.
Close lid of Universal 30 ml container.
Storage of Bacteria
Insert Universal 30 ml container into 37° C. Stuart compact orbital incubator
Set incubator at 150 RPM.
Store culture for 16 hours.
Remove 30 ml Universal container from incubator.
Bacterial growth is indicated by the nutrient broth solution becoming turbid compared to sterile nutrient broth.
If broth solution is still clear, discard and do not use.
Broth cultures cannot be stored and must be disposed of after use.

Bacteria and Bacteriophages

Bacteria and bacteriophages were acquired from internal stores. All bacteria and bacteriophages used in this study are detailed in Table 2. All bacteria were cultured in accordance with the instructions contained in the relevant SOP

TABLE 2

Bacteria and bacteriophages used in this study.

| Bacteria | Medium | Lytic Bacteriophage |
|---|---|---|
| *P. aeruginosa* NC2000 | Nutrient Agar/ Broth | ϕLIN24 |

Source of water samples

Sea water sample was sourced from Troon beach and fresh water sample was sourced from Drumpellier Lochs, Scotland, UK.

Preparation of Cellulose

Cellulose powder, average particle size 50 μm was utilised in this study. Cellulose powder to be treated with corona discharge was handled aseptically.

Immobilisation of bacteriophages onto cellulose

Cellulose powder was placed on the corona discharge table as detailed in the Immobilisation SOP. A bacteriophage solution of concentration of $1\times10^7$ PFU/ml was prepared for immobilisation. Cellulose was treated by 2× corona discharge treatments at 7.5 kV and a 10 ml bacteriophage solution was aseptically applied to the material. Cellulose powder was vacuum filtered to remove any excess bacteriophages in solution.

Preparation of 96 well plate with immobilised & non-immobilised bacteriophage in sea and fresh water environments.

Each well of the plate was filled with 200 μl final volume with equivalent volume/weight of free bacteriophages/immobilised bacteriophages 0.2 g.

Storage of samples

Each 96 well plate was incubated at 40° C. for the duration of the study to indicate an accelerated time course. 96 well plates were only removed prior to sampling.

Sampling of Bacteriophage survival

Each sample was tested in triplicate by adding the contents of a single well to 9 ml of nutrient broth and 1 ml liquid culture of the host bacterium *Pseudomonas aeruginosa* NCO2000. Samples were incubated at 37° C. for two hours in an orbital incubator. After incubation samples were filtered using 0.2 μm filters and serial diluted 1/10 using PBS for dilution to concentrations of $1\times10^{-1}$-$1\times10^{-8}$. A plaque assay was performed using the soft agar overlay method, 200 μl of each concentration including 'neat' concentration was plated on nutrient agar plates before being inoculated. Plates were incubated at 37° C. overnight in LEEC compact incubator. Following incubation visible plaques were counted and PFU/ml was determined.

EXAMPLE 2

The data shown in FIG. 2 demonstrate that immobilised bacteriophages were more resistant to UV exposure than free bacteriophages.

EXAMPLE 3

FIG. 3 shows the storage stability of *Peptobacterium* single phage immobilised onto cellulose. In this example the preparation was stored in liquid (PBS), at 4° C. in single-use aliquots.

FIG. 4 shows the storage stability of *Peptobacterium* single phage immobilised onto copolymer beads. In contrast to FIG. 3, above, the copolymer beads were stored at 4° C. in single-use aliquots but were stored under dry conditions.

FIG. 5 shows the relative degree of survival (i.e. stability) of free and immobilised bacteriophage when exposed to stress conditions. The stress conditions used are set out below:

i. Wet—4 weeks at 4° C.

ii. Dry—4 weeks at 4° C.

iii. 30 seconds UV exposure iv. 1 minute at 85° C.

Figure 1:
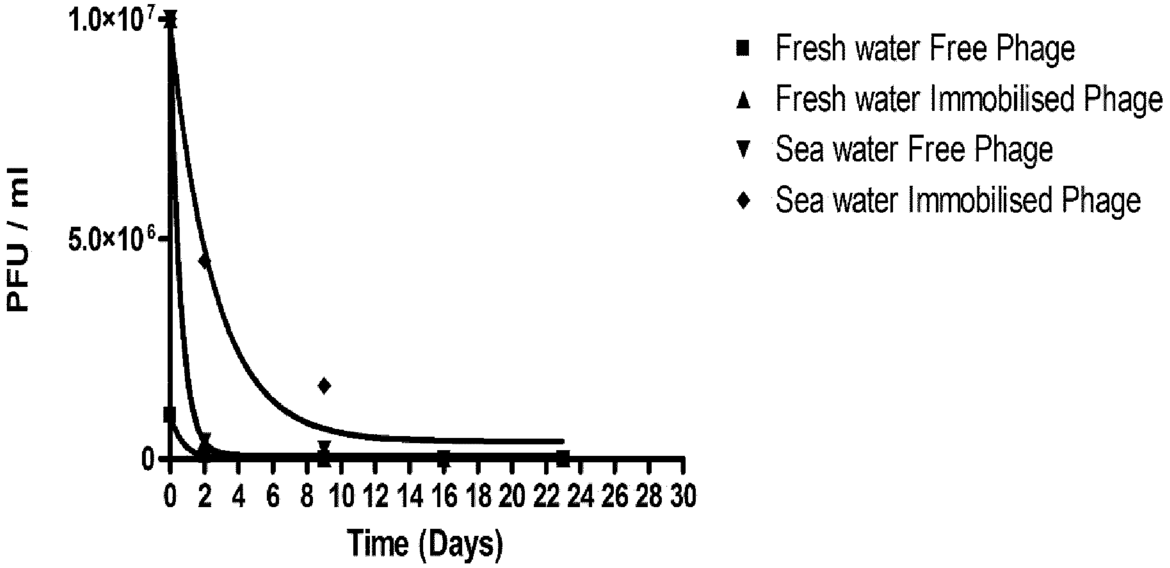
Figure 2:
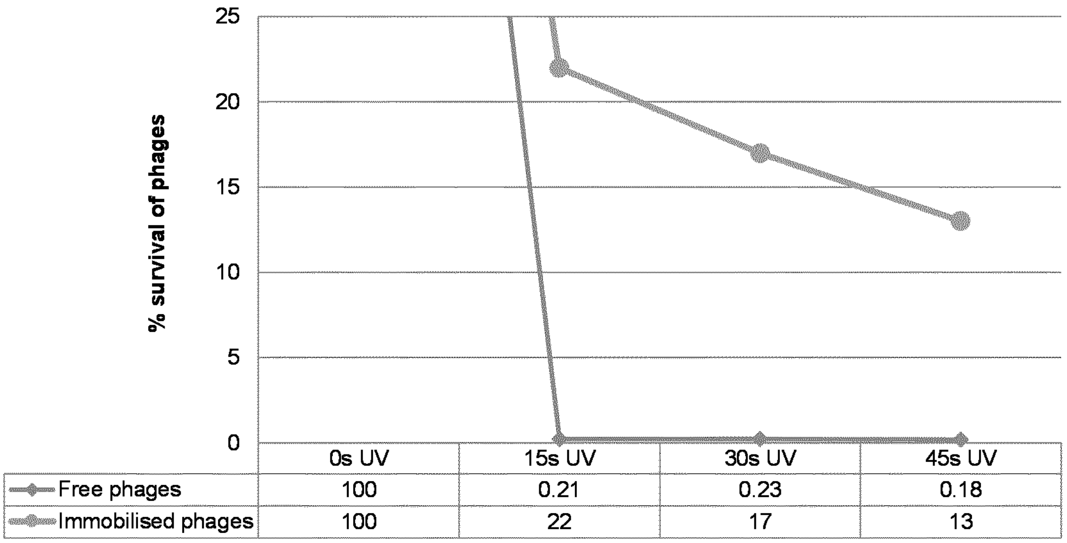
Figure 3:
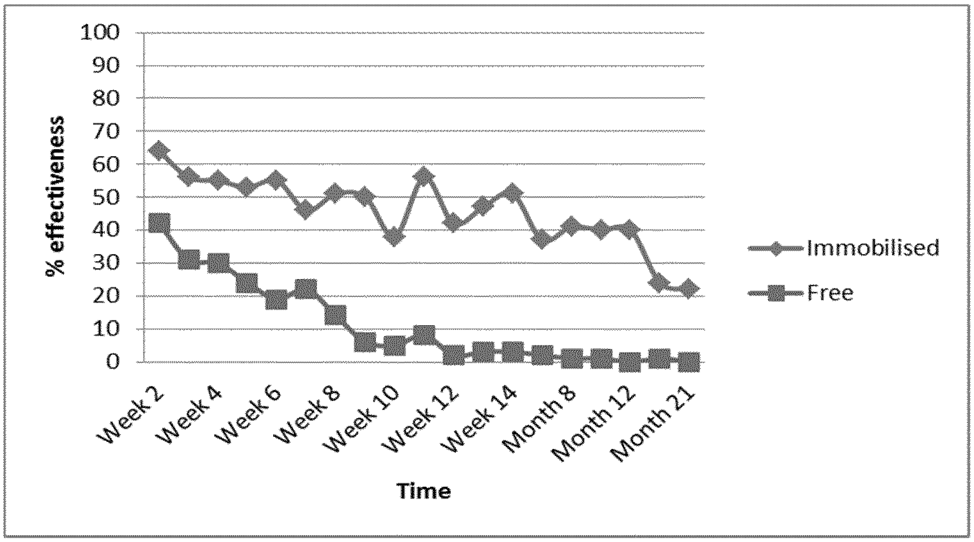
FIGS. 3 to 6 show stability under storage conditions of preparations comprising covalently attached bacteriophage under various conditions.
Figure 4:
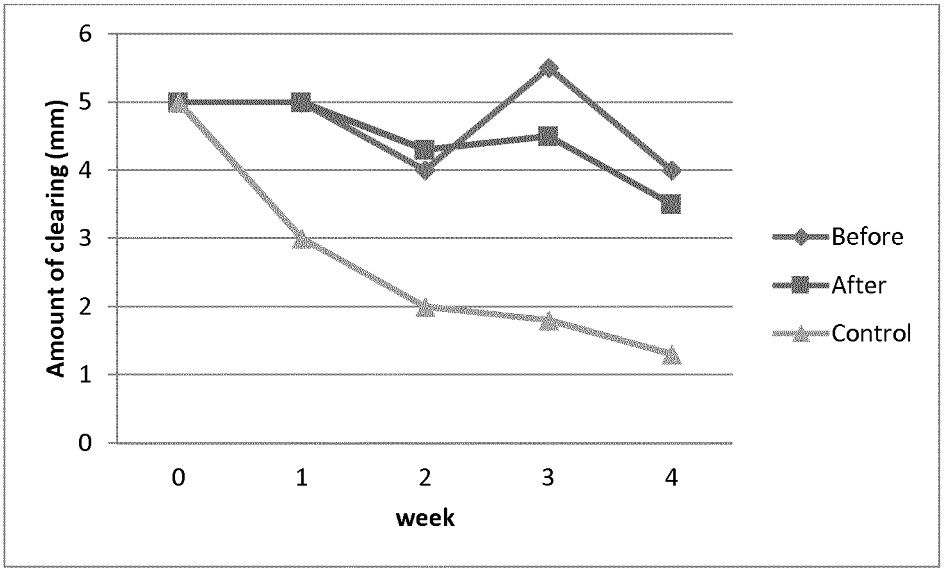
Figure 5:
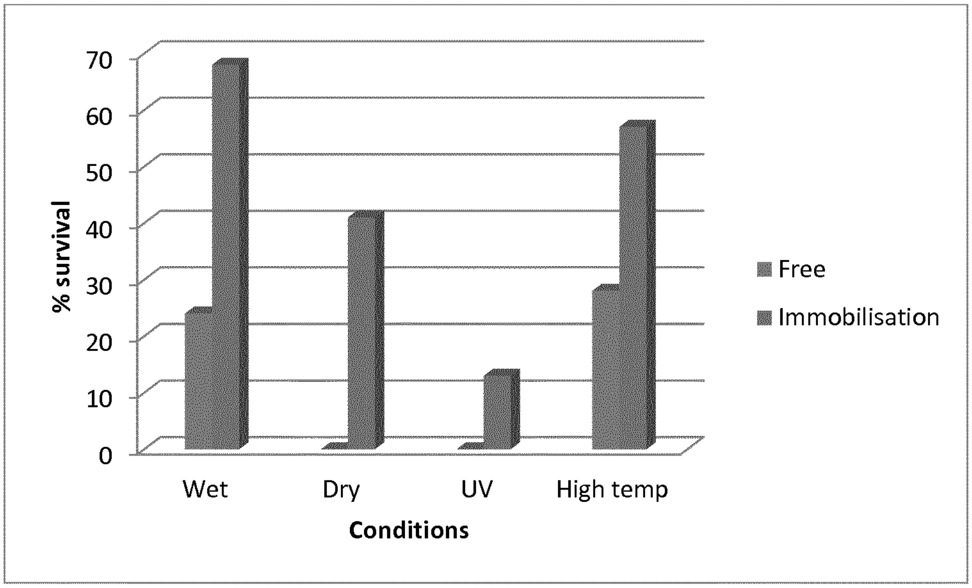
Figure 6:
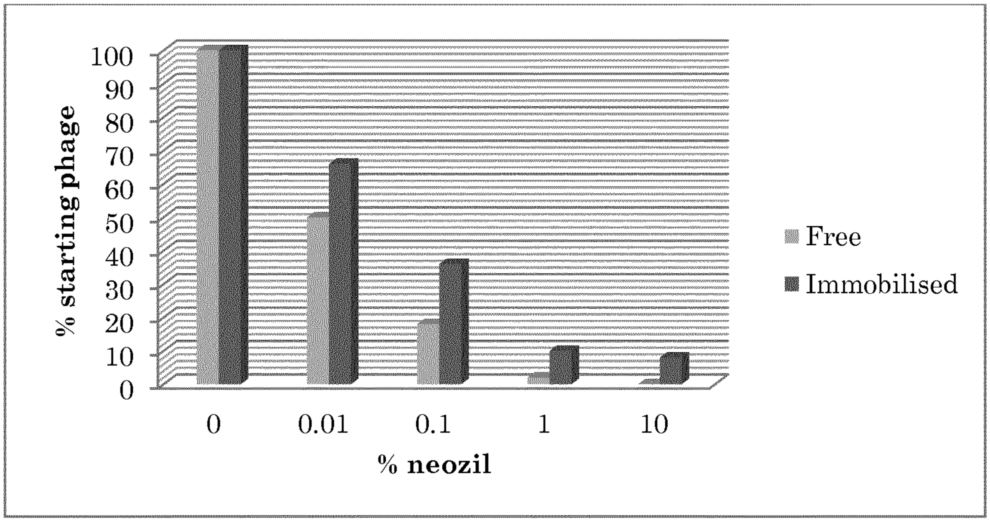

FIG. 6 shows the storage stability of free and immobilised bacteriophage potato stored in the presence of the plant antifungal agent Neozil. Storage was in PBS with Neozil at 4° C. overnight.

Table 3 shows the activity of bacteriophage covalently attached to various substrates after periods of storage—significant activity was maintained in all cases.

TABLE 3

| Material | Storage conditions | Repeat use | Host | Phage | Start Date | End Date/Last tested | Activity Maintained |
|---|---|---|---|---|---|---|---|
| Nylon squares | Dry 4° C. | Yes | *S. aurues* | K | 1 Feb. 2011 | 4 Feb. 2013 (2 yrs 3 days) | Yes |
| Copolymer 1 mm beads | Moist 4° C. | No | *P. aeruginosa* | S1 | 22 Mar. 2012 | 22 May 2013 (1 yr 2 mths) | Yes |
| Cellulose | Wet 4° C. | No | *Peptobacterium* | FP01 | 11 Mar. 2011 | 3 Jun. 2013 (2 yrs 3 mth) | Yes |
| Cellulose | Dry 4° C. | No | *Peptobacterium* | FP01 | 13 Sep. 2011 | 3 Sep. 2012 (1 year 3 months) | Yes |
| Alginate | Moist 4° C. | No | *Salmonella* | Shield | 1 May 2012 | 1 Jun. 2012 (1 months) | Yes |

EXAMPLE 4

FIGS. 7 to 11 show stability of preparations comprising covalently attached bacteriophage in soil.

Figure 7:
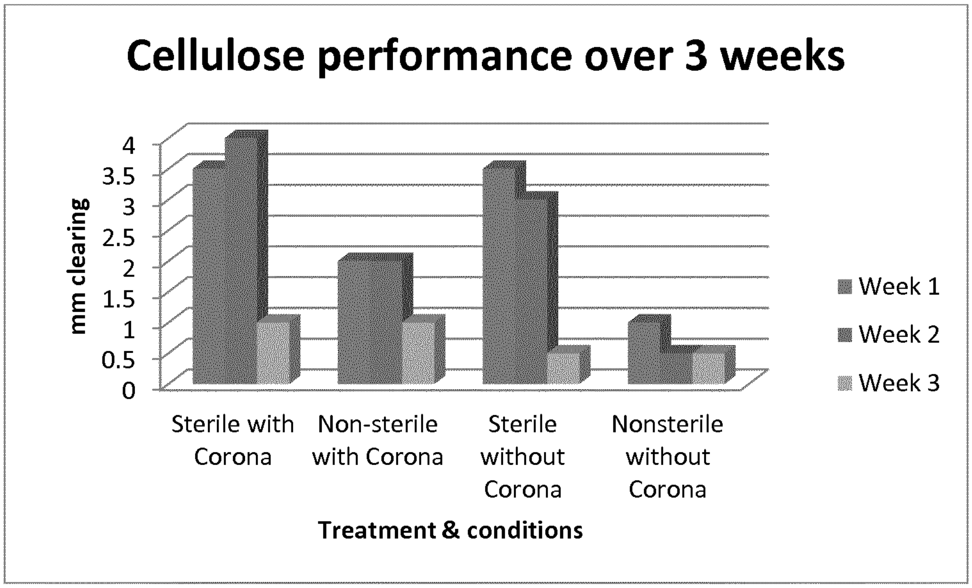
Figure 8:
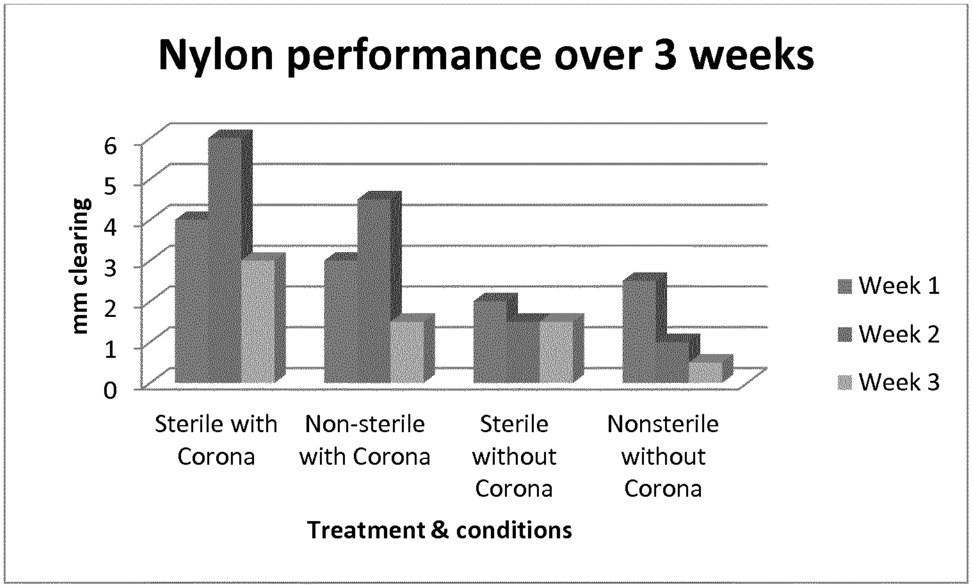

FIGS. 7 and 8 show the survival of free and bacteriophage immobilised onto cellulose and nylon strips, respectively, incubated in sterile and non-sterile soil samples. The tests were conducted at room temperature using single-use cellulose or nylon strips.

Figure 9:
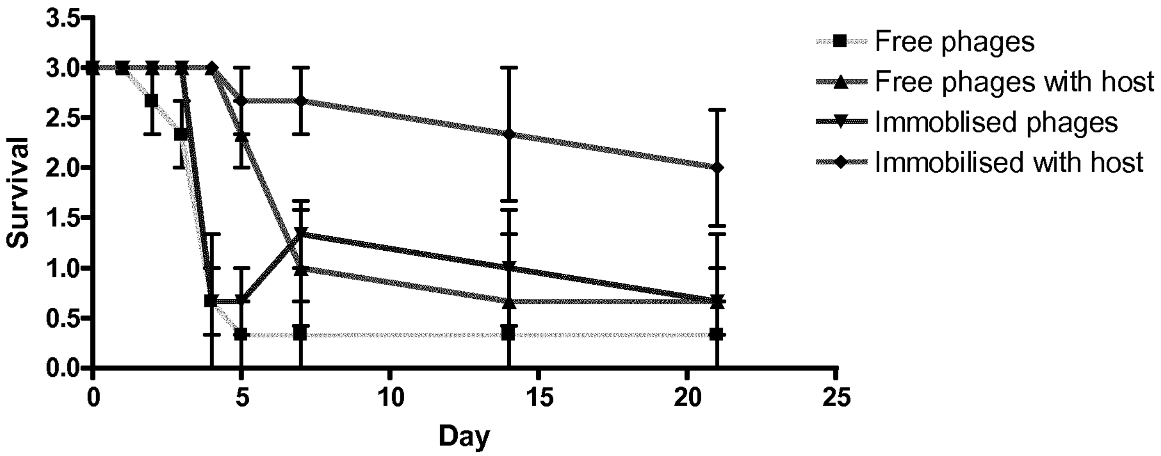
Figure 10:
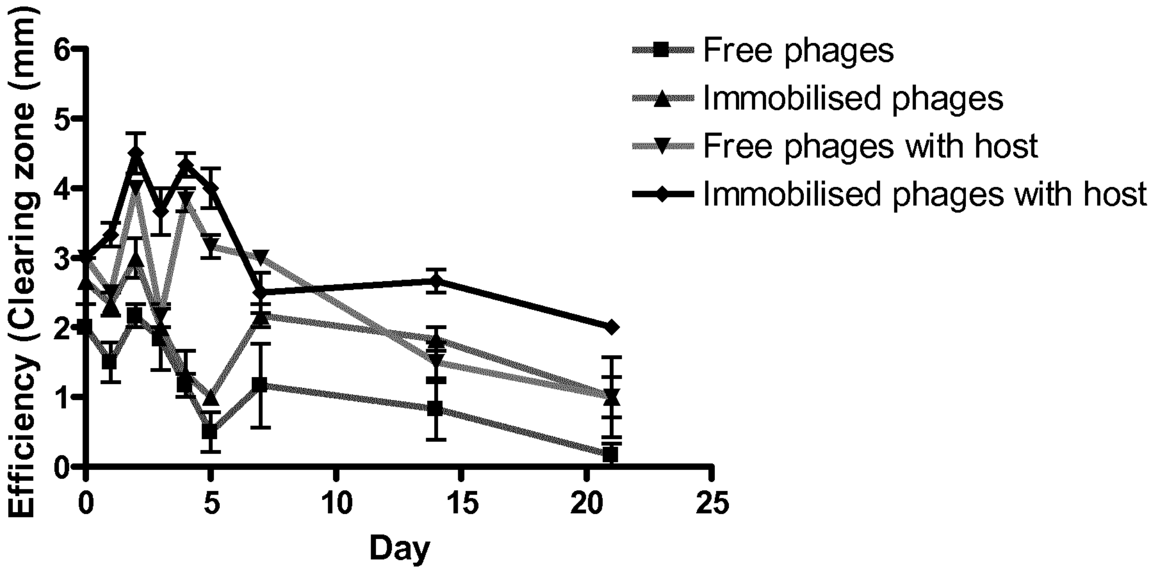

FIG. 9 shows the survival of *Peptobacterium* phage treated cellulose powder following incubation in non-sterile soil. FIG. 10 shows the antibacterial activity and hence the efficiency/effectiveness of the surviving phage. These tests were conducted at room temperature using *Peptobacterium* as a host.

Figure 11:
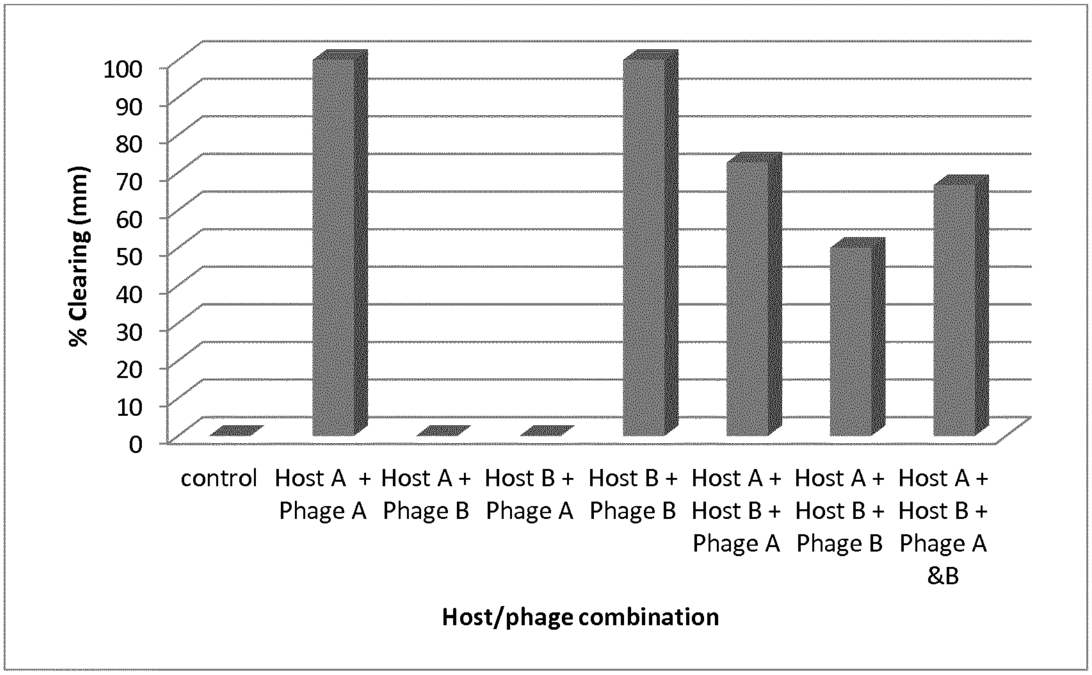

FIG. 11 shows the degree of antibacterial activity displayed when multiple bacteriophage types are immobilised on nylon in the presence of susceptible and non-susceptible host bacteria, i.e. both host and non-host bacteria are exposed to bacteriophage.

Figure 12:
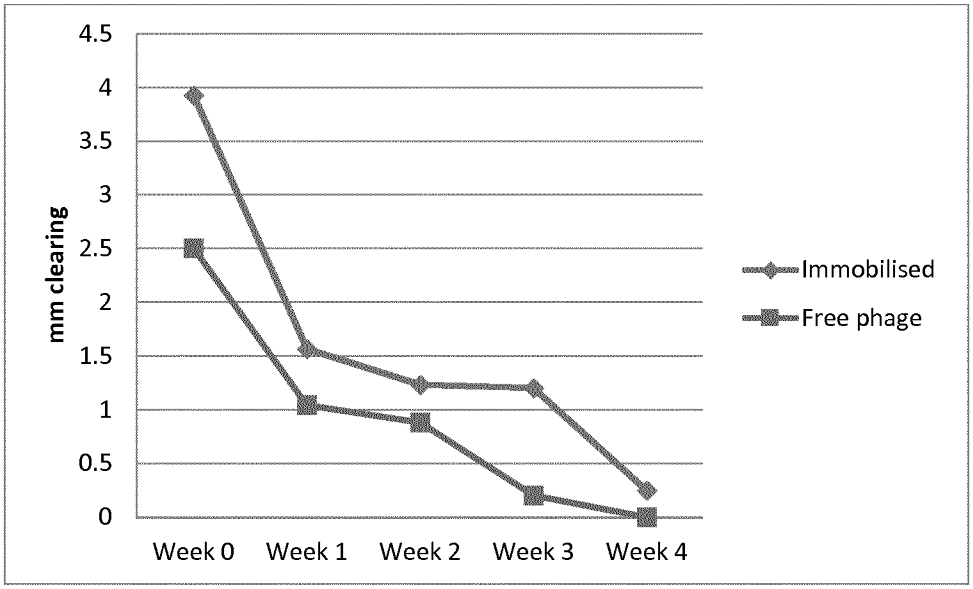

FIG. 12 shows the antibacterial activity of *Salmonella* bacteriophage immobilised onto alginate sheets. The tests were carried out using alginate sheets that were stored under dry conditions at 4° C.

EXAMPLE 5

Shrimp Feed

Feed pellets for shrimp were made as follows:

A formulation of proteins, carbohydrates, fats, minerals and vitamins comprising 182 g/kg fish meal, 200 g/kg rice pollard, 300 g/kg mill mix, 118 g/kg wheat flour, 185 g/kg coconut meal and 15 g/kg vitamin and mineral premix was thoroughly mixed in a twin shaft mixer.

A pulverizer was used to grind the mixture into a fine powder.

A conditioner was then used to expose the fine powder to a high pressure (150 psi) steam for 30 minutes. This increased the moisture content of the powder, as well as beginning to convert the starch into a readily digestible form.

The conditioned powder then entered a pellet mill set to produce pellets of 1.5 mm diameter.

The pellets were then subjected to a second conditioning step in order to facilitate binding of the starch and/or gluten in the pellet. This step dramatically increased the stability of the pellet in water.

The pellets were then cooled and dried. Dried pellets were subsequently sprayed with an aqueous suspension of bacteriophage covalently attached to nylon particles of average diameter 100 microns at a concentration of $10^9$ CFU $ml^{-1}$ allowed to dry and then processed into containers.

EXAMPLE 6

Fish Feed

Feed pellets for fish were made as follows:

A formulation of proteins, carbohydrates, fats, minerals and vitamins comprising 201 g/kg fish meal, 11 g/kg fish oil, 251 g/kg rice bran, 254 g/kg mill mix, 150 g/kg copra meal, 118 g/kg broken rice, 10 g/kg wheat flour and 5 g/kg vitamin and mineral premix was thoroughly mixed in a twin shaft mixer.

A pulverizer was used to grind the mixture into a fine powder.

A conditioner was then used to expose the fine powder to a high pressure (150 psi) steam for 30 minutes.

The conditioned powder then entered a pellet mill set to produce pellets of 5 mm diameter.

The pellets were then cooled, and dried. Dried pellets were subsequently sprayed with an aqueous suspension of bacteriophage covalently attached to cellulose particles of average diameter 50 microns at a concentration of $10^9$ CFU $ml^{-1}$ allowed to dry and then processed into containers.

EXAMPLE 7

Fish Pellets with Bacteriophage Covalently Attached

Fish food pellets based on wheat germ (composition: wheat germ, derivatives of vegetable origin, fishmeal and fish derivatives, yeasts, vegetable protein extracts, molluscs and crustacean, vitamins and minerals) were subjected to two passes through a flat bed corona machine at 7.5KV. Pellets were immediately sprayed with bacteriophage solution ($1\times10^7$ pfu/mL of Lin24) and air dried, and stored for two weeks at room temperature.

A lawn of *Camplyobacter jejuni* (ATCC12851) was prepared on Petri dishes and fragmented fish pellets retrieved from storage and placed on the surface. These were incubated at 37C for 36 hours.

Figure 13:
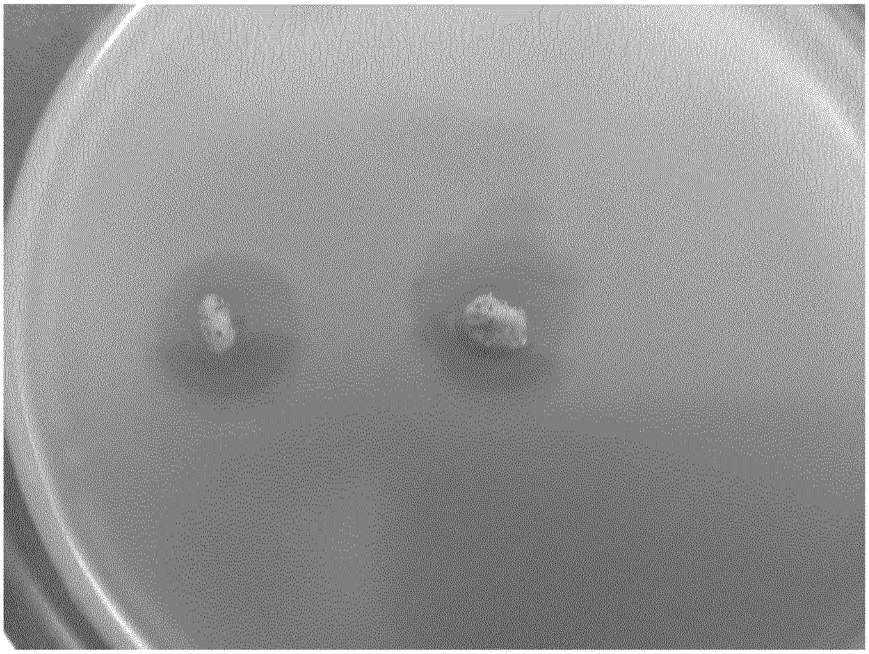

Examination of the dishes showed clearing zones around the pellet fragments, illustrated in FIG. 13. Pellets treated similarly without corona treatment were inactive (not shown) with no visible zones of clearing.

The experiment was repeated with Maize based pellets (maize derivatives of vegetable origin, fishmeal and fish derivatives, yeasts, vitamins and minerals and Spirulina), with similar results (not shown).

EXAMPLE 8

Treatment of *Vibrio* Infection of Shrimp

We developed the following protocols for treatment of *Vibrio* infections of shrimp.

Isolation of Bacteriophages Displaying Lytic Activity against *Vibrio parahaemolyticus*

The isolation of bacteriophages displaying lytic activity against *V. parahaemolyticus* is undertaken using 3 methods. Environmental samples are added directly to a *V. parahaemolyticus* agar overlay and also incubated at 37° C. for 9 h with a culture of *V. parahaemolyticus*. *V. parahaemolyticus* samples are also subjected to 1 mg/mL of mitomycin C to induce bacteriophage replication.

The presence of lytic bacteriophages is confirmed by the formation of clear plaques in a *V. parahaemolyticus* agar overlay.

Characterisation of Bacteriophages

Each lytic bacteriophage isolated is characterised by determining the host range, efficiency of plating (EOP) burst size, growth curve, molecular characterisation and restriction analysis.

Host Range and Efficiency of Plating

Each bacteriophage is added to agar overlays of each isolated *V. parahaemolyticus* to determine the host range. The EOP is determined by adding samples of a series of dilution factors to agar overlays of each isolated *V. parahaemolyticus*.

Measurement of Burst Size and Growth Curves

The burst size of each bacteriophage is determined for each *V. parahaemolyticus* isolated by incubation of a co-culture of bacteria and bacteriophage. Samples are taken at different time points to establish the number of bacteria and the number of bacteriophages remaining in solution. The burst size is calculated using the following calculation:

Burst size=(Number of bacteriophages during stationary period)/(Number of bacteriophages during lag period)

Restriction Analysis

Bacteriophage DNA is subjected to digestion by restriction enzymes to ensure that genetically identical bacteriophages are used in the bacteriophage cocktail.

Testing of Antimicrobial Activity

Tank tests are used to measure the activity of immobilised bacteriophage on *V. parahaemolyticus*. This system consists of sterile salt water inoculated with a known bacterial concentration and a tank containing supplements to replicate pond conditions. The bacteria are added to salt water containing a known concentration of immobilised bacteriophages.

Multiplicity of infection (MOI) is varied to determine the impact at different concentrations (Table 4).

TABLE 4

| Tank test MOI | | |
|---|---|---|
| MOI | Bacteriophages (pfu/mL) | Bacteria (cfu/mL) |
| 10 | $1 \times 10^7$ | $1 \times 10^6$ |
| 1 | $1 \times 10^6$ | $1 \times 10^6$ |
| 0.1 | $1 \times 10^5$ | $1 \times 10^6$ |
| 0.01 | $1 \times 10^4$ | $1 \times 10^6$ |

Outcomes and Success Criteria

The following are the identified outcomes:

A bacterial culture bank containing 3 pathogenic *V. parahaemolyticus* strains

Two fully characterised bacteriophages displaying lytic activity to both *V. parahaemolyticus* strains Each bacteriophage and a bacteriophage cocktail immobilised onto cellulose and shrimp feed and tested for anti-microbial activity on an agar overlay and tank tests.

A minimum of a 2 log reduction in bacteria observed by immobilised bacteriophage in each tank test.

Laboratory and Tank Testing

The aim of this stage is to further exemplify the effectiveness of the immobilised bacteriophage cocktail at treating *V. parahaemolyticus* by undertaking additional laboratory testing and by undertaking a tank test containing live shrimp.

Shelf life Testing

The long term shelf life of the immobilised bacteriophage formula is assessed at different storage temperatures using standard methods. This determines the recommended storage conditions and shelf life of a final product.

Infection Model with Live Shrimp

Shrimp are added to separate tanks and subjected to 3 different concentrations of *V. parahaemolyticus*. This determines the concentration required to elicit EMS pathology. Shrimps are assessed for *V. parahaemolyticus* infection of the hepatopancreas by observing differences in hepatopancreas size, overall weight vs controls and overall mortality.

Tank Test with Live Shrimp

To assess the efficacy of treatment options, shrimp are fed a specific concentration of feed containing immobilised bacteriophage and a specific concentration of cellulose containing immobilised bacteriophage. Treated shrimps are exposed to an infectious dose of *V. parahaemolyticus*. Shrimps are assessed for *V. parahaemolyticus* infection of the hepatopancreas, differences in hepatopancreas size and overall weight vs controls, and overall mortality.

Procedures

Shelf Life Testing

Immobilised material is stored at 4° C., ambient room temperature, and at 30° C. to represent a tropical climate. The shelf life of free bacteriophage solution stored at each temperature is also compared. Each material and solution are added to agar overlays of all *V. parahaemolyticus* isolates. Antimicrobial activity is confirmed by the presence of a zone of inhibition of bacterial growth around the material. Material is sampled at different time points until antimicrobial activity ceases.

Infection Model with Live Shrimp

A total of 20 *L. vannamei* shrimp are used for the infection model. A total of 5 shrimp are exposed to different concentrations of *V. parahaemolyticus*. Each shrimp is kept in an individual tank. The concentrations are $1\times10^4$ CFU, $1\times10^2$ CFU and 10 CFU representing sub lethal doses. *V. parahaemolyticus* is introduced using ingestion of shrimp food particles, reverse gavage or direct injection.

Tank Test

A total of 5 replicates containing 10 post larval stage *L. vannamei* shrimp are exposed to shrimp feed with immobilised bacteriophage and cellulose with immobilised bacteriophage. A total of 5 replicates containing 10 post larval stage *L. vannamei* shrimp are also exposed to free bacteriophage added to shrimp feed and free bacteriophage added to cellulose. All treatments are dried and incubated for 7 days at room temperature before treatment.

After a treatment dose, the shrimp are then exposed to an infectious dose of *V. parahaemolyticus* as determined in the infection model. *V. parahaemolyticus* is delivered by ingestion of shrimp food particles, reverse gavage or through direct injection. Shrimp mortality is recorded daily and upon mortality the hepatopancreas of each shrimp is measured and sampled for bacterial counts and the presence of haemocytic nodules and hyaline necrosis of the tissue. Treated shrimp are compared to control groups consisting of shrimp exposed to *V. parahaemolyticus* alone and shrimp exposed to each bacteriophage treatment alone. The study is conducted for 30 days or based on the results of the infection model.

Outcomes and Success Criteria

The following are the identified outcomes:

The immobilisation protocol is optimised.

The shelf life of immobilised bacteriophage at elevated temperature, room temperature and at 4° C. is commenced and determined throughout the study.

The effectiveness of immobilised bacteriophage as a biocontrol is confirmed with live shrimp.

Success is defined as a statistically significant reduction in differences in hepatopancreas size and overall weight vs controls, and shrimp mortailty or hepatopancreas pathology when exposed to immobilised bacteriophage treatment.

EXAMPLE 9

Saltwater shrimp were exposed to *Vibrio parahaemolyticus*, the causative agent of AHPND (Acute hepatopancreas necrosis disorder). This infection was then treated by giving the shrimp a feed comprising immobilised bacteriophages active against *V. parahaemolyticus.*

Acquisition and Culture of Microorganisms and Bacteriophages

*V. parahaemolyticus* strain designation 0004 has displayed mortality in shrimp and is available for immediate work. *V. parahaemolyticus* 0004 will be routinely cultured using the methods detailed above. Bacteriophage DRGS has been shown to have lytic activity against *V. parahaemolyticus* 0004 and will be used for the study.

Shrimp Tank Setup

Two 17 litre saltwater tanks were set up with a mature biological filter and water movement provided by a circulation pump. Salt water with a salinity of 34 ppm purified using reverse osmosis and maintained at a temperature of 26° C. was used for the study.

Saltwater Shrimp Survival and Food Uptake

A total of 20 *Thor amboinensis* saltwater shrimp were acquired and 10 specimens were added to 2 separate tanks. Shrimp feed measuring 1 mm in diameter manufactured by CP foods was used in this study and the uptake of the feed by shrimp was assessed for 3 days.

Immobilisation of Bacteriophage

CP feed material was disinfected by exposure to UV light for 30 min before being twice exposed to corona treatments at 7.5 kV. A total of 10 ml of a $1\times10^8$PFU stock of bacteriophage was applied to 20 grams of feed material. Each material was then washed 3 times in sterile distilled water and dried in a laminar flow cabinet. Antimicrobial activity was assessed using an agar overlay and using the culture test to determine antimicrobial activity.

*Thor Amboinensis* Care and Feeding Schedule

Shrimp were regularly fed twice a day on feed equivalent to 5% of their estimated body weight. One tank was fed untreated CP feed and the other tank was fed feed comprising immobilised bacteriophage. Feeding occurred for 3 days before inoculation of the tanks with *V. parahaemolyticus* and was maintained during inoculation.

Inoculation and Assessment of Shrimp Health

Each tank was dosed with a culture of *V. parahaemolyticus* to make a final volume of $1\times10^8$ CFU/mL in the tank. Shrimp health was assessed after 6 hours of exposure and each shrimp was given a rating using the criteria described in Table 5. Health was then assessed daily. A sample of tank water was taken daily to provide counts of bacteria in each tank. For the bacterial counts, a sample of tank water was subjected to 8×1⁄10 serial dilutions and a sample plated onto TCBS agar. For the bacteriophage counts, a tank water sample was passed through a 0.2 μM filter and subjected to a 8×1⁄10 serial dilutions and a 100 μl sample was added to a *V. parahaemolyticus* 0004 3% NaCl soft nutrient agar overlay.

TABLE 5

Shrimp health assessment ratings

| Rating | Description |
|---|---|
| A | Alive, regular movement, no observable ailments, appetite. |
| B | Alive, limited movement, limited response to stimuli, appetite. |
| C | Alive, unable to move/stand, very limited response to stimuli, no appetite. |
| D | Dead. |

Results

Figure 14:
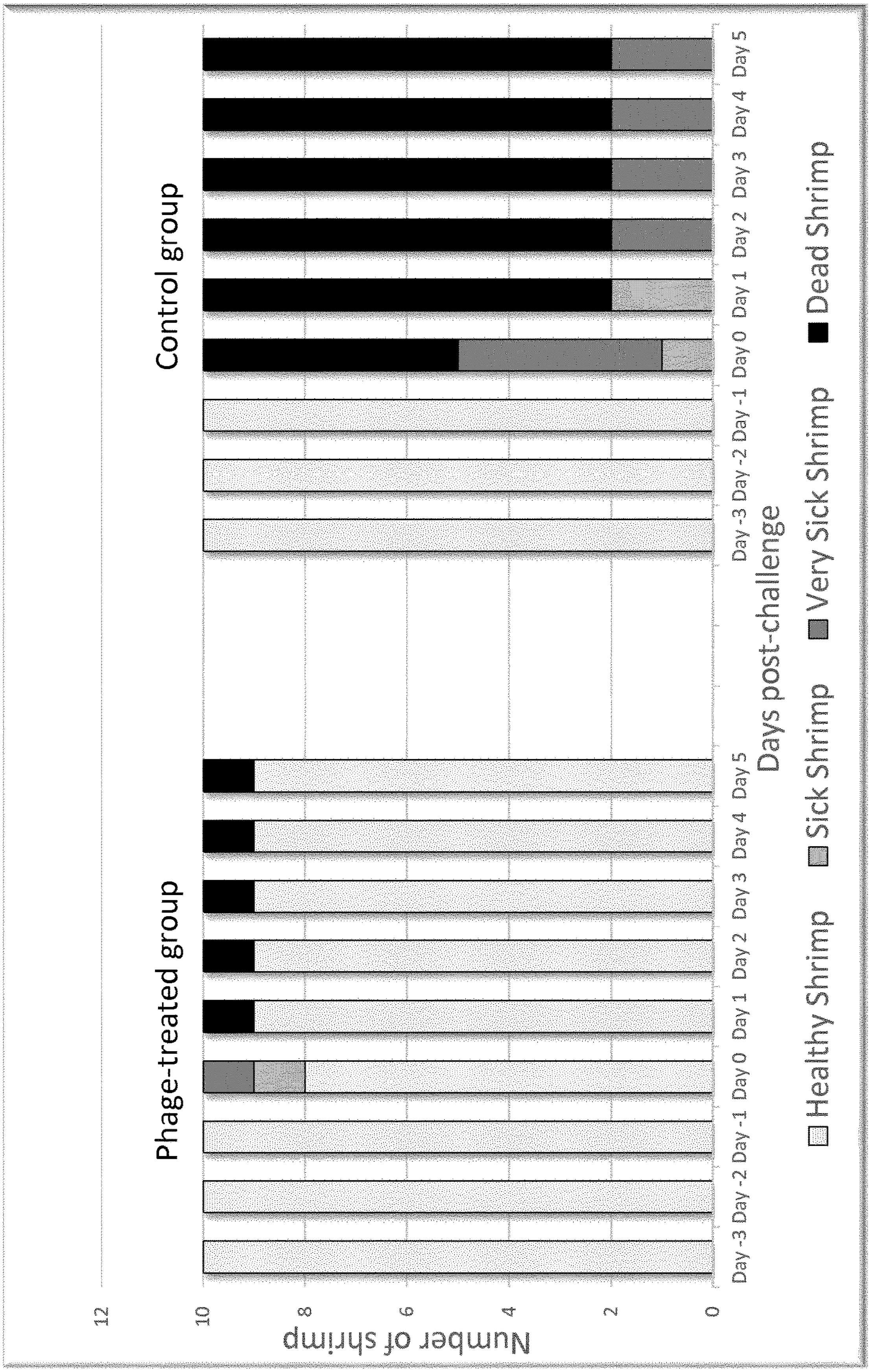

All material containing immobilised bacteriophage displayed antimicrobial activity and resulted in a 2 log reduction when directly exposed to the bacteria in solution. No shrimp casualties were observed before inoculation with *V. parahaemolyticus* in both tanks (Table 6; FIG. 14). A total of 8 shrimp casualties were observed in the no treatment control and a total of 1 shrimp casualty was observed in the treatment tank (Table 6; FIG. 14). The surviving shrimp in the no treatment control tank were observed to have increased morbidity compared to the surviving shrimp in the treatment tank (Table 6; FIG. 14). No significant difference was observed in the number of bacteria in each tank and significantly more bacteriophage was isolated from the treatment tank (Table 7).

TABLE 6

Health assessments of *Thor amboinensis* used in this study

| Time | No Treatment Control | Immobilised Bacteriophage Treatment |
|---|---|---|
| Day 0 | A - 10 | A - 10 |
| | B - 0 | B - 0 |
| | C - 0 | C - 0 |
| | D - 0 | D - 0 |
| Day 1 | A - 10 | A - 10 |
| | B - 0 | B - 0 |
| | C - 0 | C - 0 |
| | D - 0 | D - 0 |
| Day 2 | A - 10 | A - 10 |
| | B - 0 | B - 0 |
| | C - 0 | C - 0 |
| | D - 0 | D - 0 |
| Day 3 (Inoculation) | A - 0 | A - 8 |
| | B - 1 | B - 1 |
| | C - 4 | C - 1 |
| | D - 5 | D - 0 |
| Day 4 | A - 0 | A - 9 |
| | B - 2 | B - 0 |
| | C - 0 | C - 0 |
| | D - 8 | D - 1 |
| Day 5 | A - 0 | A - 9 |
| | B - 0 | B - 0 |
| | C - 2 | C - 0 |
| | D - 8 | D - 1 |

TABLE 7

Number of Bacteria and bacteriophages recovered from each tank.

| | Number of *V. parahaemolyticus* (CFU/mL) | |
|---|---|---|
| Test Tank | Day 3 | Day 4 |
| No Treatment Control | $1 \times 10^6$ | $1.2 \times 10^4$ |
| Immobilised Bacteriophage Tank | $1.1 \times 10^6$ | $1 \times 10^4$ |

Conclusions

Immobilised bacteriophage on shrimp feed confers a protective effect on *Thor amboinensis* shrimp exposed to a large infectious dose of a pathogenic strain of *V. parahaemolyticus* that is known to cause AHPND in aquacultured shrimp. No significant difference was found in *V. parahaemolyticus* numbers in the tank water which indicates the protective effect is happening locally at the site of infection. At the conclusion of the trial, 3 shrimp were sacrificed and the presence of bacteriophages in the gut confirmed.

The invention hence provides compositions and methods for treatment of bacterial infections in aquaculture, generally of shrimp, prawns and fish.

The invention claimed is:

1. Feed for crustaceans or fish, comprising bacteriophage covalently attached to a particle for treating bacterial infection in fish or crustaceans, wherein the particle comprises carbohydrate or protein to which bacteriophage are covalently attached, wherein the bacteriophage is covalently attached to the particle in an irreversible manner, wherein the covalently attached bacteriophage cannot diffuse from its point of attachment to the carbohydrate or protein.

2. Feed according to claim 1, wherein the particle or pellet is made of edible material.

3. Feed according to claim 2, wherein the bacteriophage are active against infection by *Vibrio* bacteria species in crustaceans.

4. Feed according to claim 2, wherein the bacteriophage are active against infection by *Vibrio, Aeromonas, Yersinia, Moritella, Rickettsia, Piscirickettsia, Lactococcus, Pseudomonas, Flavobacterium* or *Photobacterium* bacteria species in fish.

5. A method of making fish or crustacean feed comprising mixing bacteriophages covalently attached to particles into feed components, to produce feed comprising said particles, wherein the particles comprise carbohydrate or protein to which bacteriophage are covalently attached.

6. A method according to claim 5, comprising:

(a) combining feed components to form a mixture, (b) heat treating the mixture to (i) increase its moisture content, or (ii) heat and cook the mixture, or (iii) both (i) and (ii), (c) cooling the treated mixture, and (c) subsequently adding the particles to the treated and cooled mixture and forming pellets of feed comprising bacteriophages covalently attached to particles.

7. A method according to claim 5, comprising adding the particles to formed feed pellets.

8. Feed for crustaceans or fish comprising edible feed components to which bacteriophage is covalently attached, for treating bacterial infection in fish or crustaceans, wherein the edible feed components comprise carbohydrate or protein to which bacteriophage are covalently attached, wherein the bacteriophage is covalently attached to the edible feed components in an irreversible manner, wherein the covalently attached bacteriophage cannot diffuse from its point of attachment to the carbohydrate or protein.

9. Feed according to claim 8, in the form of pellets.

10. A method of making fish or crustacean feed comprising covalently attaching bacteriophage to feed pellets, wherein the pellets comprise carbohydrate or protein to which bacteriophage are covalently attached.

11. A method according to claim 10, comprising forming pellets from feed components, activating the pellets and combining activated pellets with a solution or suspension of bacteriophage.

12. A method according to claim 7, comprising adding the particles to formed feed pellets by spraying pellets with a solution or suspension of the particles.

13. Feed according to claim 9, wherein the pellets are of diameter up to 25 mm.

* * * * *